(12) United States Patent
Wallace et al.

(10) Patent No.: US 6,425,914 B1
(45) Date of Patent: *Jul. 30, 2002

(54) FAST-DETACHING ELECTRICALLY INSULATED IMPLANT

(75) Inventors: Michael P. Wallace, Pleasanton; Mehran Bashiri, San Carlos; Chad C. Roue, Livermore, all of CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/668,033

(22) Filed: Sep. 21, 2000

Related U.S. Application Data

(63) Continuation of application No. 08/920,526, filed on Aug. 29, 1997, now Pat. No. 6,156,061.

(51) Int. Cl.[7] ............................ A61F 2/06; A61M 29/00
(52) U.S. Cl. ...................... 623/1.11; 606/195; 606/200
(58) Field of Search .......................... 623/1.11, 11, 12; 606/200, 195, 198

(56) References Cited

U.S. PATENT DOCUMENTS

| | | |
|---|---|---|
| 4,010,759 A | 3/1977 | Boer |
| 4,739,768 A | 4/1988 | Engelson |
| 4,884,579 A | 12/1989 | Engelson |
| 4,945,342 A | 7/1990 | Steinemann |
| 4,994,069 A | 2/1991 | Ritchart et al. |
| 5,122,136 A | 6/1992 | Guglielmi et al. |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. et al. |
| 5,304,200 A | 4/1994 | Spaulding |
| 5,312,415 A | 5/1994 | Palermo |
| 5,350,397 A | 9/1994 | Palermo et al. |
| 5,354,295 A | 10/1994 | Guglielmi et al. |
| 5,356,433 A | 10/1994 | Rowland |
| 5,423,829 A | 6/1995 | Pham et al. |
| 5,522,836 A | 6/1996 | Palermo |
| 5,540,680 A | 7/1996 | Guglielmi et al. |
| 5,549,624 A | 8/1996 | Mirigian |
| 5,569,245 A | 10/1996 | Guglielmi et al. |
| 5,582,619 A | 12/1996 | Ken |
| 5,609,629 A | 3/1997 | Fearnot et al. |

(List continued on next page.)

FOREIGN PATENT DOCUMENTS

| | | |
|---|---|---|
| EP | 0 719 522 A1 | 7/1996 |
| EP | 0 826 342 A1 | 3/1998 |
| JP | 7-265431 | 10/1995 |
| WO | WO 97/48351 | 12/1997 |
| WO | WO 98/02100 | 1/1998 |
| WO | WO 98/04198 | 2/1998 |
| WO | WO 98/04315 | 2/1998 |

Primary Examiner—Dinh X. Nguyen
Assistant Examiner—Cheryl L. Miller
(74) Attorney, Agent, or Firm—Lyon & Lyon (57) ABSTRACT

This is an implant for placement in the human body and an assembly for so placing that implant. Most desirably, it is an implant for use in the vasculature of the human body and is used to occlude some space in that vasculature as a portion of a treatment regimen. The implant itself is preferably a component of a deployment device using an electrolytically severable joint. The implant component is at least partially covered with a highly resistive or insulative covering. The highly resistive or insulative layer or covering appears to enhance the susceptibility of the electrolytic joint to quick erosion and thus detachment of the implant. Although the implant itself is preferably a vaso-occlusive device, it may instead be a stent, a vena cava filter, or other implant which may be installed in this manner. The implant may be independently coated with insulative or resistive material or may be formed using a material with such as tantalum, which forms such an insulator or resistor in situ.

20 Claims, 5 Drawing Sheets

U.S. PATENT DOCUMENTS

| | | |
|---|---|---|
| 5,624,449 A | 4/1997 | Pham et al. |
| 5,624,461 A | 4/1997 | Mariant |
| 5,634,942 A | 6/1997 | Chevillon et al. |
| 5,643,254 A | 7/1997 | Scheldrup et al. |
| 5,645,082 A | 7/1997 | Sung et al. |
| 5,649,951 A | 7/1997 | Davidson |
| 5,733,294 A | 3/1998 | Forber et al. |
| 5,743,905 A | 4/1998 | Eder et al. |
| 5,759,161 A | 6/1998 | Ogawa et al. |
| 5,800,454 A | 9/1998 | Jacobsen et al. |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,895,391 A | 4/1999 | Farnholtz |
| 5,911,717 A | 6/1999 | Jacobsen |
| 5,916,235 A | 6/1999 | Guglielmi |
| 5,919,187 A | 7/1999 | Guglielmi et al. |
| 5,925,037 A | 7/1999 | Guglielmi et al. |
| 5,925,060 A | 7/1999 | Forber |
| 5,925,062 A | 7/1999 | Purdy |
| 5,928,226 A | 7/1999 | Guglielmi et al. |
| 5,941,888 A | 8/1999 | Wallace et al. |
| 5,944,714 A | 8/1999 | Guglielmi et al. |
| 5,947,962 A | 9/1999 | Guglielmi et al. |
| 5,947,963 A | 9/1999 | Guglielmi |
| 5,976,126 A | 11/1999 | Guglielmi |
| 6,010,498 A | 1/2000 | Guglielmi |

FAST-DETACHING ELECTRICALLY INSULATED IMPLANT

RELATED PATENT APPLICATION

This application is a continuation of U.S. patent application Ser. No. 08/920,526, filed Aug. 29, 1997, now U.S. Pat. No. 6,156,061 the entirety of which is hereby incorporated by reference.

FIELD OF THE INVENTION

This invention is an implant for placement in the human body and an assembly for so placing that implant. Most desirably, it is an implant for use in the vasculature of the human body and is used to occlude some space in that vasculature as a portion of a treatment regimen. The implant itself is preferably a component of a deployment device using an electrolytically severable joint. The implant component is at least partially covered with a highly resistive or insulative covering. The highly resistive or insulative layer or covering appears to enhance the susceptibility of the electrolytic joint to quick erosion and thus detachment of the implant. Although the implant itself is preferably a vaso-occlusive device, it may instead be a stent, a vena cava filter, or other implant which may be installed in this manner. The implant may be independently coated with insulative or resistive material or may be formed using a material with such as tantalum, which forms such an insulator or resistor in situ.

BACKGROUND OF THE INVENTION

Implants may be placed in the human body for a wide variety of reasons. For instance, stents are placed in a number of different lumens in the body. They may be placed in arteries to cover vascular lesions or to provide patency to the vessel. Stents are also placed in biliary ducts to prevent them from kinking or collapsing. Grafts may be used with stents to promote growth of endotbelial tissue within those vessels.

Vena cava filters are implanted in the body, typically in the vena cava, to catch thrombus which are sloughed off from other sites within the body and which may be in the blood passing through the chosen site.

Vaso-occlusive devices or implants are used for a wide variety of reasons. They are often used for treatment of intra-vascular aneurysms. This is to say that the treatment involves the placement of a vaso-occlusive device in an aneurysm to cause the formation of a clot and eventually of a collagenous mass containing the vaso-occlusive device. These occlusions seal and fill the aneurysm thereby preventing the weakened wall of the aneurysm from being exposed to the pulsing blood pressure of the open vascular lumen.

Treatment of aneurysms in this fashion is significant improvement over the surgical method typically involved. The surgical or extravascular approach is a common treatment of intra-cranial berry aneurysm; it is straightforward but fairly traumatic. The method involves removing of portion of the cranium and locating the aneurysm. The neck of the aneurysm is closed typically by applying a specially sized clip to the neck of the aneurysm. The surgeon may choose to perform a suture ligation of the neck or wrap the entire aneurysm. Each of these procedures is performed by an very intrusive invasion into the body and is performed from the outside of the aneurysm or target site. General anesthesia, craniotomy, brain retraction, and a placement of clip around the neck of the aneurysm all are traumatic. The surgical procedure is often delayed while waiting for the patient to stabilize medically. For this reason, many patients die from the underlying disease prior to the initiation of the surgical procedure.

Another procedure—the extra-intravascular approach—involves surgically exposing or stereotaxically reaching an aneurysm with a probe. The wall of the aneurysm is perforated from the outside and various techniques are used to occlude the interior of the aneurysm to prevent its rebleeding. The techniques used to occlude the aneurysm include electro-thrombosis, adhesive embolization, hoghair embolization, and ferromagnetic thrombosis. These procedures are discussed in U.S. Pat. No. 5,122,136 to Guglielmi et al., the entirety of which is incorporated by reference.

Guglielmi et al. further describes an endovascular procedure which is at once the most elegant and least invasive. The procedure described in that patent includes a step in which the interior of the aneurysm is entered by the use of guidewire such as those in Engelson, U.S. Pat. No. 4,884,579 and a catheter as in Engelson, U.S. Pat. No. 4,739,768. These patents described devices utilizing guidewires and catheters which allow access to aneurysms from remote parts of the body. Typically, these catheters enter the vasculature through an artery in the groin. The Guglielmi et al system uses catheters and guidewires which have a very flexible distal regions and supporting midsections which allow the combinations to be steerable to the region of the aneurysm. That is to say that the guidewire is first steered for a portion of the route to the aneurysm and the catheter is slid up over that guidewire until it reaches a point near the distal end of the guidewire. By steps, the catheter and guidewire are then placed at the mouth of the aneurysm. The catheter is introduced into the aneurysm and vaso-occlusive or embolism-forming devices may be delivered through the lumen.

Various vaso-occlusive devices are introduced through the noted microcatheters to close the aneurysm site. In some instances, a small balloon may be introduced into the aneurysm where it is inflated, detached, and left to occlude the aneurysm. Balloons are becoming less in favor because of the difficulty in introducing the balloon into the aneurysm sac, the possibility of aneurysm rupture due to over-inflation of the balloon within the aneurysm, and the inherent risk associated with the traction produced when detaching the balloon.

Another desirable embolism-forming device which may be introduced into aneurysm using end of vascular placement procedure is found in U.S. Pat. No. 4,994,069 to Ritchart et al. In that patent are described various devices—typically platinum/tungsten alloy coils having very small diameters—which may be introduced into the aneurysm through a catheter such as those described in the Engelson patents above. These coils are often made of wire having a diameter of 2–6 mils. The coil diameter is often 10–30 mils. These soft, flexible coils, may be of any length desirable and appropriate for the site to be occluded. After these vaso-occlusive coils are placed in, e.g., a berry aneurysm, they first cause a formation of an embolic mass. This initial mass is shortly thereafter complemented with a collagenous material which significantly lessens the potential for aneurysm rupture.

There are variety of other vaso-occlusive devices, typically coils which may be delivered to the vascular site in a variety of ways, e.g., by mechanically detaching them from the delivery device. A significant number of these devices are described in patents owned by Target Therapeutics, Inc. For instance:

U.S. Pat. No. 5,234,437, to Sepetka shows a method of unscrewing a helically wound coil from a pusher having interlocking surfaces.

U.S. Pat. No. 5,250,071, to Palermo shows an embolic coil assembly using interlocking clasps both on the pusher and on the embolic coil.

U.S. Pat. No. 5,261,916, to Engelson shows a combination pusher/vaso-occlusive coil assembly joined by an interlocking ball and keyway type coupling.

U.S. Pat. No. 5,304,195, to Twyford et al., shows a pusher/vaso-occlusive coil assembly having a fixed proximally extending wire carrying a ball on its proximal end and a pusher having a similar end which two tips are interlocked and disengaged when expelled from the distal tip of the catheter.

U.S. Pat. No. 5,312,415, to Palermo shows a method for discharging numerous coils from a single pusher by using a guidewire which has a section capable of interconnecting with the interior of a helically wound coil.

U.S. Pat. No. 5,350,397, to Palermo et al. shows a pusher having a throat at its distal end and a pusher through its axis. The pusher throat holds onto the end of an embolic coil and releases that coil upon pushing the axially placed pusher wire against member found on the proximal end of the vaso-occlusive coil.

Other mechanically detachable embolism forming devices are known in the art.

Each of the patents listed herein is specifically incorporated by reference.

Guglielmi et al. shows an embolism forming device and procedure for using that device which, instead of a mechanical joint, uses an electrolytically severable joint. Specifically, Guglielmi et al. desirably places a finely wound platinum coil into a vascular cavity such as an aneurysm. The coil is delivered endovascularly using a catheter such as those described above. After placement in the aneurysm, the coil is severed from its insertion core wire by the application of a small electric current to that core wire. The deliverable coils are said to be made of a platinum material. They may be 1–50 cm or longer as is necessary. Proximal of the embolic coil, as noted above, is a core wire which is typically stainless steel. The core wire is used to push the platinum embolic coil into vascular site to be occluded.

Other variations of the Guglielmi et al. technology are found in U.S. Pat. No. 5,354,295.

None of the references described above teach or suggests an implant having a highly resistive or insulative layer on at least a portion of its exterior surface which is flexibly attached to an electrolytically severable delivery joint.

SUMMARY OF THE INVENTION

This invention is an implant which is at least partially coated with an insulative material. The implant may be a vaso-occlusive device, stent, vena cava filter, or any other implant which may be delivered via a catheter. Desirably, the device includes a core wire having a distal tip, which distal tip may be introduced into the selected site. The core wire is attached to the distal tip or implant in such a way that it may be electrolytically detached by application of a current to the core wire.

The improvement involves the use of an insulative or highly resistive covering on at least a portion of the implant. The resistive covering is preferably one which is formed in situ from the material making up the implant. This insulative or highly resistive layer appears to focus the current flow through the sacrificial electrolytic joint and thereby improves the rate at which detachment occurs.

DESCRIPTION OF THE INVENTION

As noted above, the Guglielmi et al. system for deploying an implant into the human body uses a core wire, an electrolytic sacrificial joint, and the implant to be deployed. A power supply is needed to provide power for electrolysis of the joint. The core wire is typically insulated on its outer surface from near the proximal end of the wire to the electrolytic sacrificial joint. The implant typically forms a portion of the circuit through the body. This invention substantially removes the implant itself from that circuit, thereby apparently focusing the current flow at the electrolytic joint where it is needed.

Figure 1:
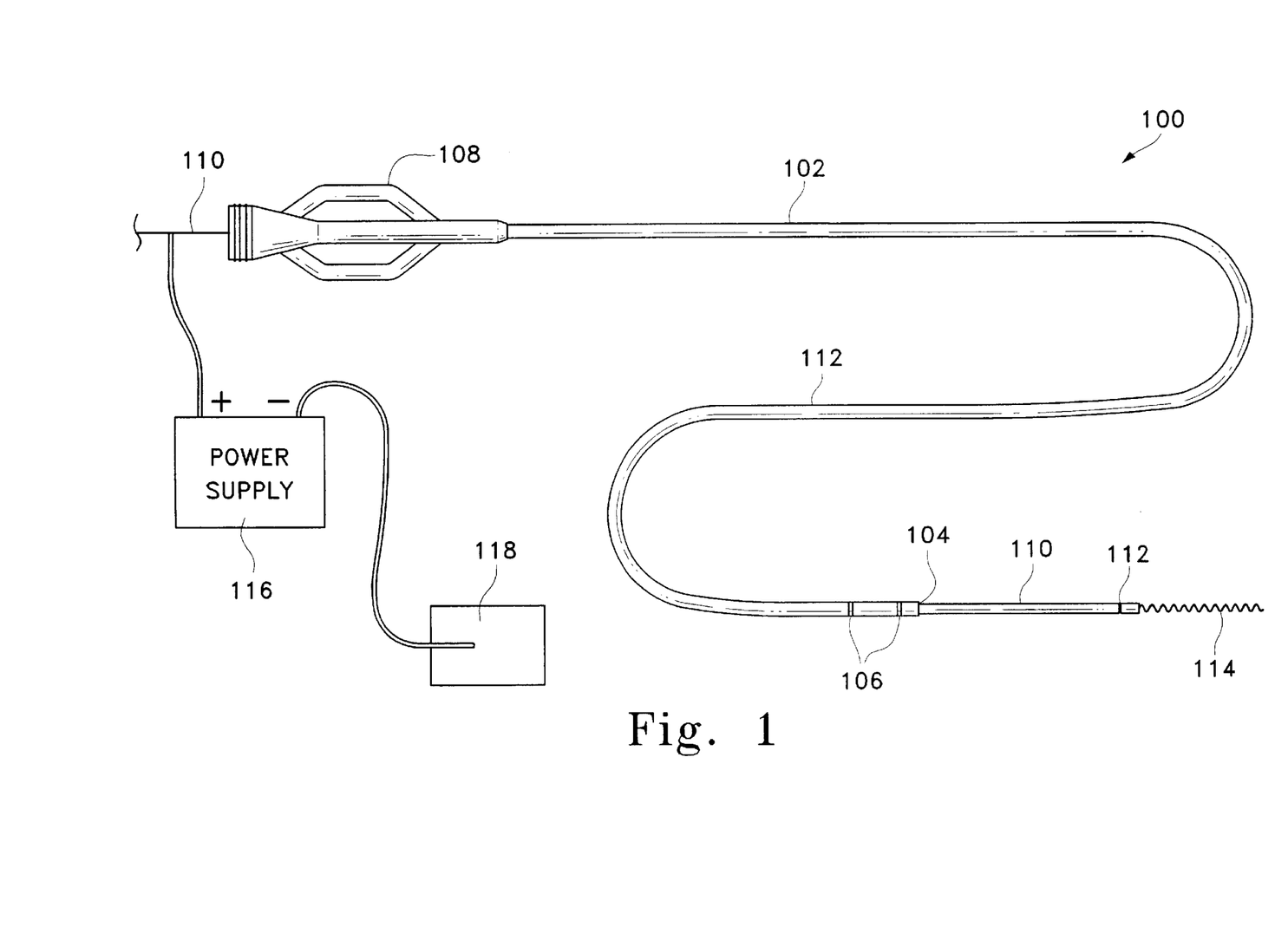
FIG. 1 shows the overall layout of a delivery system showing the typical major parts for delivering an implant using the improvement of this invention.

FIG. 1 shows a system for introducing and deploying the implant made according to the invention. The system (100) includes a catheter (102) which is made up of elongate tubular member, typically made from a polymeric material and often reinforced to provide strength or obviate kinking propensities with a coil or braid. Catheter (102) is shown with a pair of radio-opaque markers (106). The radio-opaque markers (106) allow visualization of the distal end (104) of the catheter so to compare it with the coincidence of the implant (114). Catheter (102) is also shown with a proximal fitting (108) for introduction of dyes or treatment materials. Within the lumen of catheter (102) is a core wire (110) extending both proximally of catheter (102) and distally. On the distal end of core wire (110) may be seen the electrolytic joint (112) and the implant (114). In this instance, implant (114) is a helically wound vaso-occlusive coil. Generally, all of core wire (110) is electrically insulated from a point near the proximal end of core wire (110) continuously to electrolytically severable joint (112). Electrolytically severable joint (112) is bare and is relatively more susceptible to electrolysis in an ionic solution such as blood or most other bodily fluids than is the implant (114).

The most proximal end of core wire (110) is also left bare so that power supply (116) may be attached. The other pole of the power supply (116) is typically attached to a patch (118). The patch (118) is placed on the skin to complete the circuit from the power supply (116), through the core wire (110), through electrolytic joint (112), through the ionic solution in the body, and back to a patch (118) to the power supply (116). Other return routes may be used as the designer sees fit.

Figure 2:
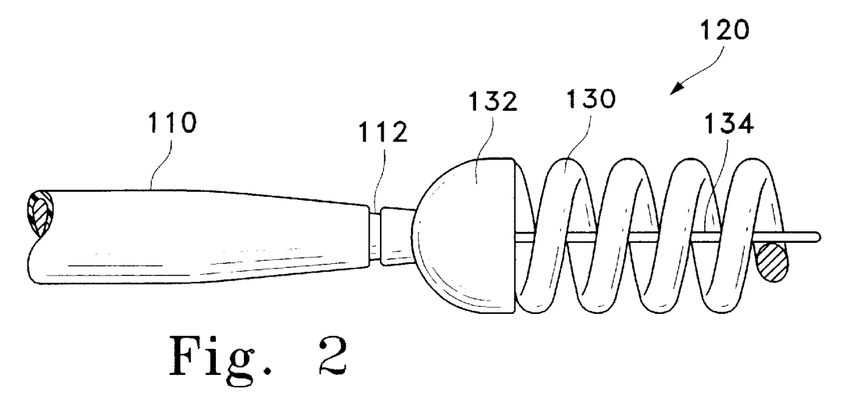
FIG. 2 shows a partial close up of a variation of the invention.

FIG. 2 shows a close-up of the more distal portion of the core wire (110) and the attached implant (120). Typically, core wire (110) will be conductive but covered with a insulative layer both proximal and distal of electrolytically severable joint (112). The interior of core wire (110) is typically electrically and physically attached to implant (120). In this variation of the invention, implant (120) is shown to be a helically wound coil (130) with an end (132) and having a stretch-resisting member (134) through its center lumen. The anti-stretch member (134) may be of any suitable material, e.g., metallic wire or polymeric threads. Preferred are polymeric threads of polypropylene or polyethyleneterephthalate, although almost any polymeric material which is formidable into a fiber is quite suitable. The stretch resisting member is simply designed to prevent the coil (130) from stretching in the event that core wire (110) must be withdrawn or repositioned to change the position of the implant (120).

The coil making up this variation of the invention is generally of a diameter in the range of 0.00025 inches and 0.006 inches. Wire of such diameter is wound into a primary form having a diameter of between 0.003 and 0.025 inches. For most neurovascular indications, the preferable primary coil diameter is preferably between 0.008 and 0.018 inches.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Central to this invention is the provision of a highly resistive or insulative layer or covering on at least a portion of implant (120). Without wishing to be bound by theory, it is believed that the covering on implant (120) prevents or lessens current flow through the implant (120) itself and concentrates the current flow through the electrolytic joint (112). Preferably, implant (120) has at least 95% of its surface area covered with the layer. The layer, which will be discussed in more detail below, should not be of a type which interferes with the formation of the occlusion, when the implant is an occlusion device. It similarly should not interfere with the other functions inherent with this specific type of implant placed distally of the electrolytically severable joint (112). That is to say that, for instance, the insulative layer should not interfere with the function of a stent by, e.g., being thrombogenic.

Figures 3A, 3B:
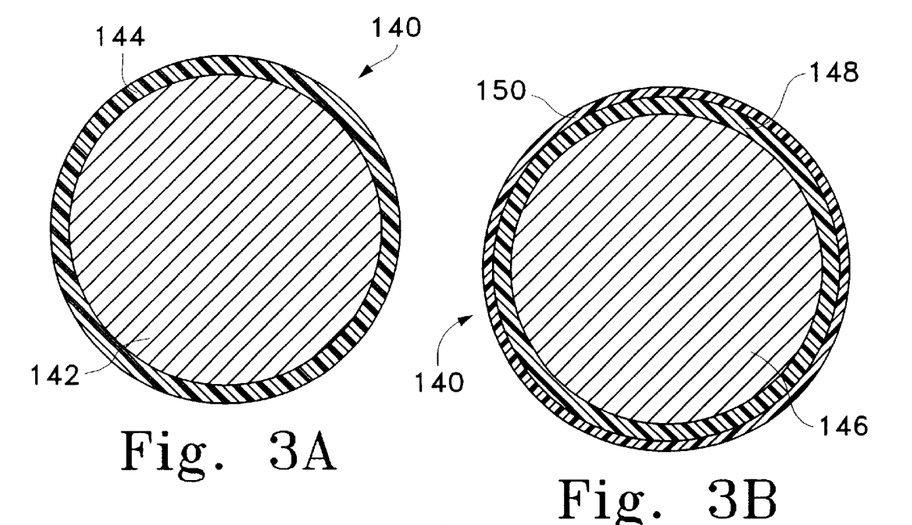
FIGS. 3A, 3B, and 3C show, respectively, cross sections depicting various manners of coating implants made according to this invention.
Figure 3C:
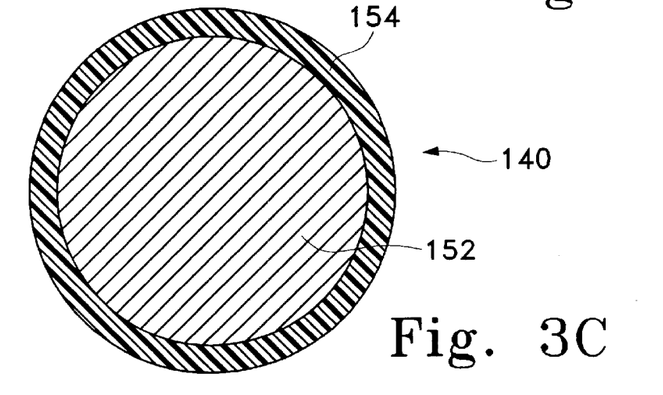

FIGS. 3A, 3B, and 3C show cross sections of the element making up the implant (140) made according to this invention. FIG. 3A shows implant (140) having a core (142) and a resistive or insulative cover (144). In this variation, the core (142) may be of an oxide-forming material. A "oxide forming material" is one which, under the imposition of an electrical current, will form an oxide skin (144), particularly in an ionic medium such as saline solution, blood, or other bodily fluids. One such material is the metal tantalum and certain of its alloys. In this instance, the device such as shown in FIG. 1 and FIG. 2 may be introduced into the body without an oxide or insulative layer. The insulative layer will form in situ upon application of a current. This is the preferred embodiment of the invention. This insulative layer, once formed, prevents current flow from the interior core (142) into the ionic medium surrounding the implant (140) once layer (144) has been formed.

The implant may be made of other insulation-forming materials or oxide forming materials including metals such as zirconium, its alloys, and related materials which form or may be made to form exterior resistive layers by, e.g., nitriding, or the like, preferably but not necessarily in situ.

Although the core (142) may be completely made of a insulation forming material as is shown in FIG. 3A, the core (146) maybe of another material, e.g., platinum or the like. As shown in FIG. 3B, a covering of an oxide or insulative forming material (148) such as tantalum or a zirconium may be plated or sputtered onto the core (146). As was the case with the variation shown in FIG. 3A, the insulative forming layer (148) will form an insulation layer (150) preferably upon application of a suitable electric current in situ but not necessarily so.

FIG. 3C shows still another variation of the inventive device in which core (152) is simply covered with an insulative material (154), which insulative material (154) is preferably inorganic in nature. For instance, to utilize an implant made of a conductive material such as stainless steel or gold and prevent or substantially lessen the flow of electrical current from the implant (140) into the surrounding ionic medium, an inorganic covering may be applied to the exterior surface. The difference between the covering (154) found in FIG. 3C and the exterior coverings found in FIGS. 3A and 3B (144, 150) is that the former coverings are capable of being formed in situ while the latter covering in FIG. 3C is not.

Figure 4:
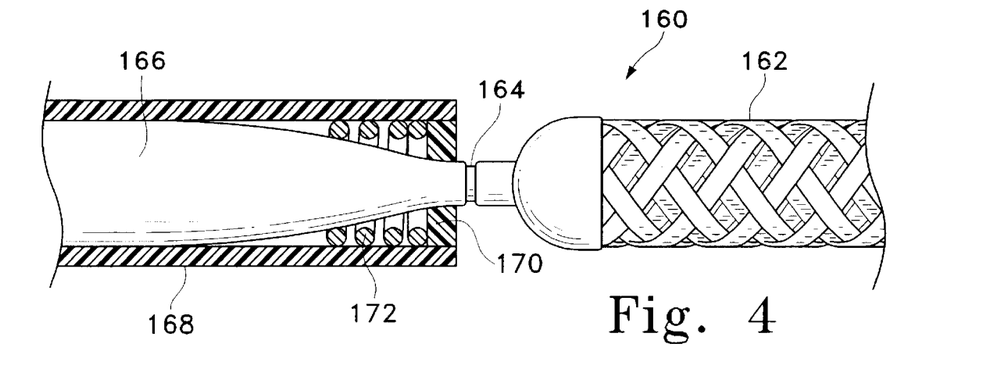
FIG. 4 shows a partial cross section of an electrolytic joint and a vaso-occlusive braid all made according to this invention.

Although the preferred variation of the invention is that found in FIG. 2 wherein a helical coil constructed of tantalum is fixably attached distally of electrolytically severable joint (112), other forms of implants are suitable. For instance, FIG. 4 shows another variation of the inventive device (160) in which the implant is a vaso-occlusive braid (162), either woven or unwoven. The electrolytically severable joint (164) is shown to be located proximally of vaso-occlusive braid (162). In this variation, the core wire (166) is insulated with a tubular member (168) and a bushing (170). A stabilizing coil (172) is also depicted on the distal end of core wire (166). Bushing (170) and covering (168) serve to electrically insulate core wire (166) from the surrounding ionic fluid. These coverings along with those found on vaso-occlusive woven braid (162) are considered to focus the electrolysis process on the electrolytically severable joint (164).

Figure 5:
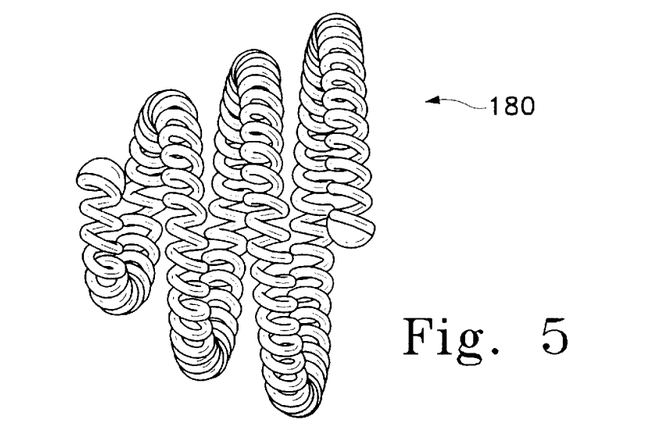
FIGS. 5 and 6 show helically wound vaso-occlusive coils having secondary shapes which may be deployed using the procedures described herein.
Figure 6:
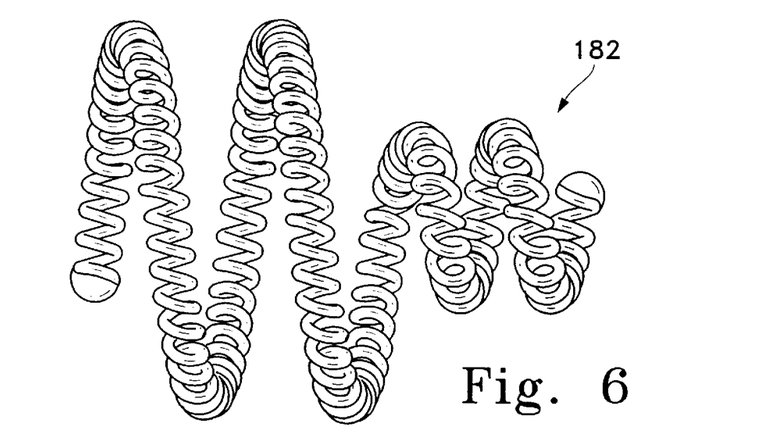

When the implant is a vaso-occlusive device, the shape of the device may be any of a number of suitable overall shapes to promote occlusion of the selected interior body space. In particular, when the implant is a helical coil, many shapes are known for treatment of particular abnormalities. FIGS. 5 and 6 show useful devices for treatment of arterio-venous malformations (AVM) and aneurysms. Specifically, FIG. 5 shows a vaso-occlusive coil which has a secondary conical shape. A "secondary" shape is meant to include any form in which a wire is first formed into a first helical form and that first helical form is wound into a second form, possibly helical. As was noted above, vaso-occlusive devices are introduced through a catheter. Pushing the vaso-occlusive device through the catheter uses that first linear configuration which approximates the shape of the interior of the catheter. Secondary shapes, such as shown in FIGS. 5 and 6, are formed when the vaso-occlusive device is allowed to exit the distal end of the catheter. The secondary shape of the vaso-occlusive device (180) shown in FIG. 5 is, as noted just above, conical in form.

FIG. 6 shows a variation (182) of the inventive device in which two sections of the catheter have different secondary diameters.

Each of the catheters described herein may also have attached fibrous materials to increase thrombogenicity.

Figure 7:
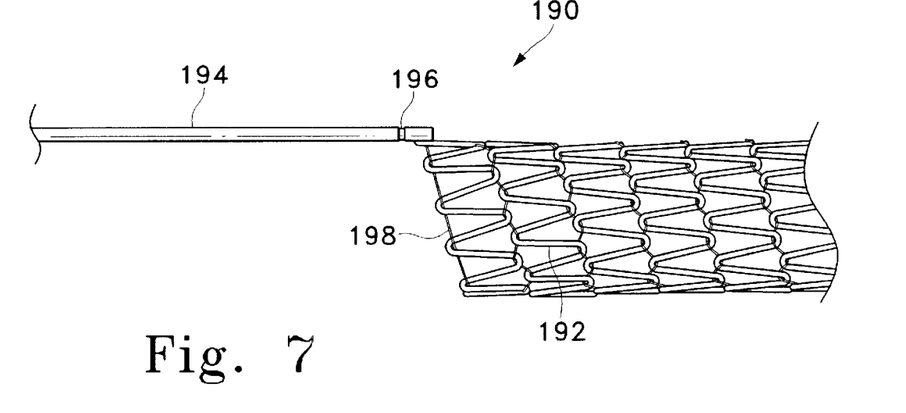
FIG. 7 shows a stent implant using the improvements of this invention.

FIG. 7 shows a variation (190) of the inventive device in which the implant is a stent (192). Core (194) is also is shown with an electrolytically erodable joint (196).

The stent shown in FIG. 7 is a variation of a self-expanding stent typically made of a super-elastic alloy material, typically a nickel-titanium alloy (e.g., nitinol), that is well known in the art. The device is shown to have a zig-zag pattern of a metallic wire which is maintained in the noted and secondary form by a filament (198) which is woven through the bends of the stent to maintain the secondary shape. The primary shape is simply the shape shown but with a significantly lower diameter. The form of the stent is not important to the invention but is only illustrative of the form an implant may take.

Figure 8:
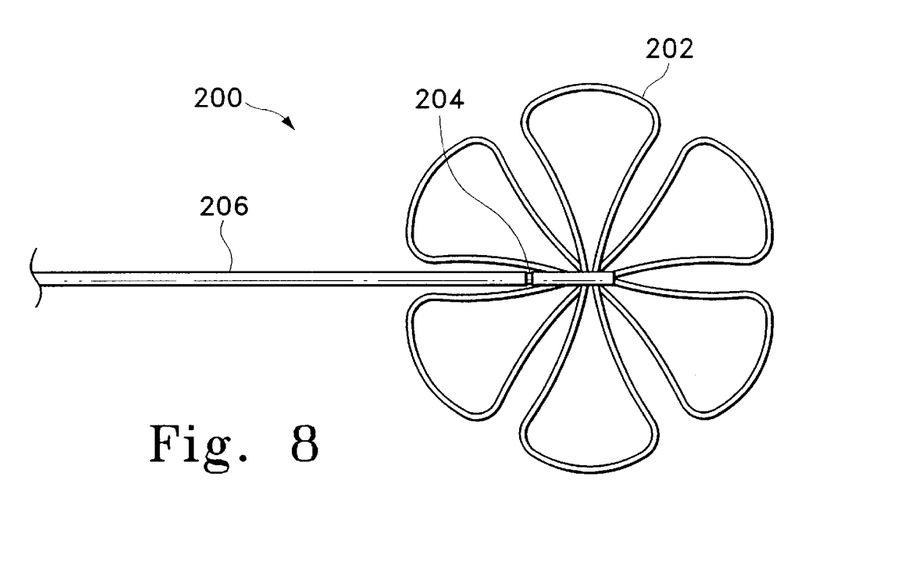
FIG. 8 shows a vena cava filter which may be deployed using the improvements of this invention.

FIG. 8 shows the expanded form of an implant (200) which may be used as a vena cava filter. Vena cava filters are well known in the art and are used to prevent the flow of blood clots distally in the vasculature. These blood clots would eventually be the site of occlusive strokes in the brain if allowed to travel distally. In any event, implant (200) shows the vena cava filter member (202), the electrolytically severable joint (204) and the push wire or core wire (206).

Figures 9A, 9B:
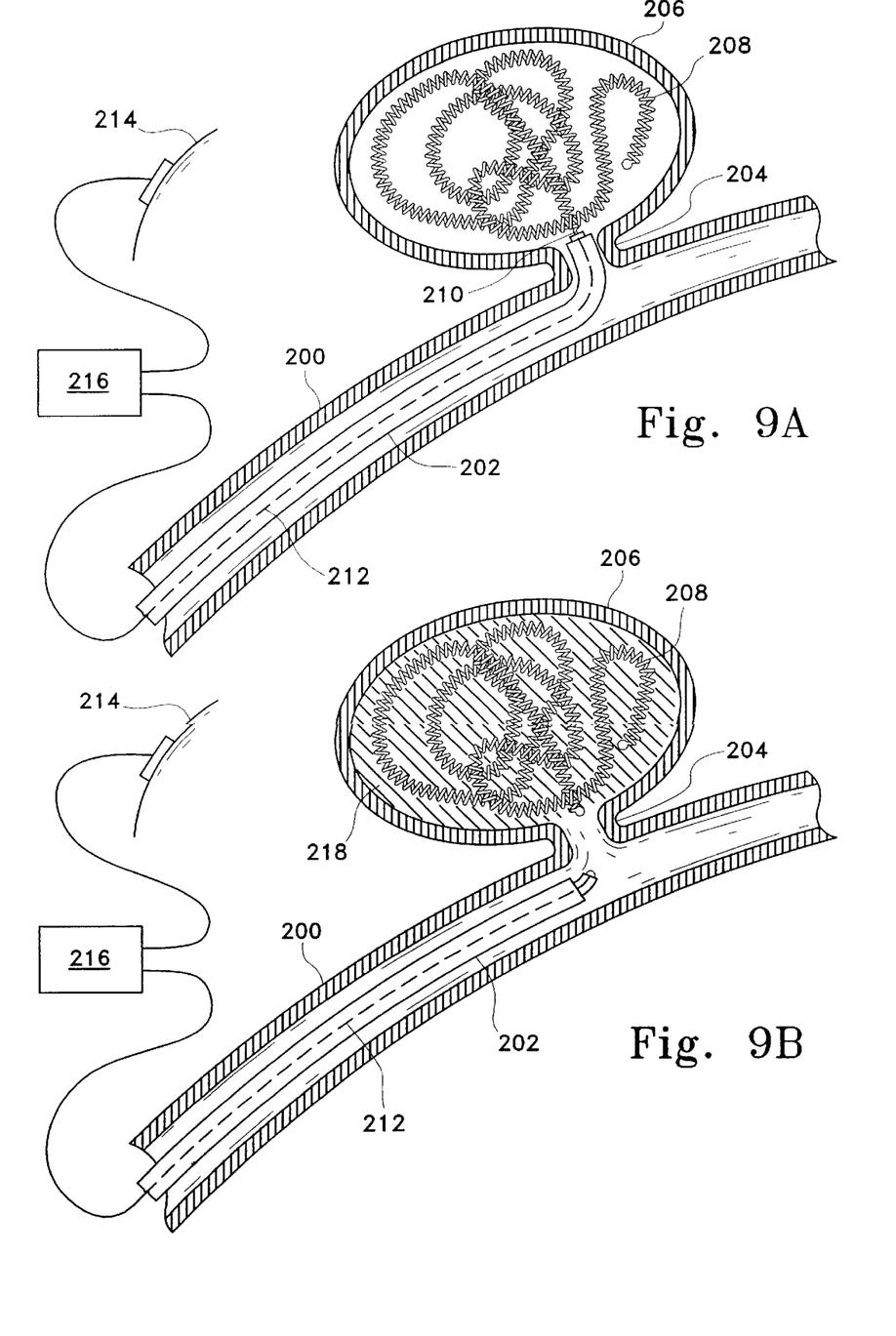
FIGS. 9A and 9B show, in schematic form, a procedure for deploying the inventive vaso-occlusive device of this invention.

FIGS. 9A and 9B show placement of the inventive devices, specifically the vaso-occlusive variations of the invention, within the human body. FIG. 9A shows the placement within a vessel (200) with a tip of catheter (202) placed near aneurysm neck (204). The aneurysm itself is nominated (206). Vaso-occlusive device (208) is fed into aneurysm (206) at least until the sacrificial link (210) (hidden within catheter (202) at this step) is exposed beyond the distal tip of catheter (202). A positive electric current of approximately 0.01–2 milliamps at 0.1–6 volts is applied to core wire (212). Thrombus is then formed within aneurysm (206). The negative pole (214) of power supply (216) is typically placed in electrical contact with the skin so to complete the circuit.

After the thrombus (218) has been formed and the aneurysm occluded, vaso-occlusive device (208) is detached from core wire (212) by electrolytic disintegration of sacrificial link (210).

After sacrificial link (210) is at least mostly dissolved by electrolytic action, typically in less than two minutes and most often in less than one minute, the core wire (212) and catheter (202) are removed from vessel (200) leaving aneurysm (206) occluded as shown in FIG. 9B.

This procedure is practiced under fluoroscopic control either with general or local anesthesia. A transfemoral catheter is typically used to treat cerebral aneurysms and is usually introduced at the groin. When the vaso-occlusive device (208) is insulated or covered with a highly resistive material as is contemplated this invention, it is not affected by electrolysis. When the core wire (212) and the pertinent portions of the supporting coils at the distal tip of the core wire (when utilized) are adequately coated with insulating coverings, only the exposed portion of the sacrificial link (210) is affected by the electrolysis.

Many alterations and modifications may be made by those having ordinary skill in this art without departing from the spirit and scope of the invention. The illustrative embodiments have been used only for the purposes of clarity and should not be taken as limiting the invention as defined by the following claims.

We claim the following:

1. A method for introducing an implant member into a selected space within the human body comprising:

placing an implant member via an attached core wire into the selected space, said implant member having a proximal end and a distal end and having an implant member core at least partially covered with an inorganic insulative covering, and detaching the implant from the core wire.

2. The method of claim 1 wherein the implant member further comprises an electrolytically severable joint attached to the implant member proximal end, the joint being relatively more susceptible to electrolysis in an ionic solution than is the implant member, and the step of detaching the implant from the core wire is accomplished electrolytically.

3. The method of claim 1 wherein the implant member at least partially comprises an oxide-forming material.

4. The method of claim 1 wherein the implant member comprises a core at least partially covered by a oxide-forming member.

5. The method of claim 2 wherein the implant member comprises a core at least partially covered by an oxide-forming material.

6. The method of claim 1 wherein the implant member comprises a stent.

7. The method of claim 1 wherein the implant member comprises a vena cava filter.

8. The method of claim 1 wherein the implant member comprises a helically wound coil.

9. The method of claim 8 wherein the coil further comprises a stretch resistant member extending at least partially from a proximal end of the coil to a distal end of the coil.

10. The method of claim 9 wherein the stretch resistant member comprises polypropylene.

11. The method member of claim 1 wherein the implant member comprises a braid.

12. A method for occluding a selected space within a human body comprising:

placing the tip of a catheter near the selected space, introducing into a lumen of said catheter a tantalum occluding member having a proximal end and a distal end and further comprising an electrolytically severable joint attached to the occluding member proximal end, the joint being relatively more susceptible to electrolysis in an ionic solution than is the occluding member, placing the occluding member into the space through the catheter tip, and electrolytically severing the joint.

13. The method of claim 12 wherein the occluding member is at least partially covered with tantalum oxide.

14. The method of claim 12 wherein the occluding member comprises a coil.

15. The method of claim 14 wherein the coil further comprises a stretch resistant member extending at least partially from a proximal end of the coil to a distal end of a coil.

16. The method of claim 12 wherein the occluding member comprises a braid.

17. A method for occluding an aneurysm comprising:

placing the tip of a catheter near the aneurysm via a blood vessel, introducing into a lumen of the catheter a vaso-occlusive coil having a proximal end and a distal end and a highly resistive or insulative layer on at least a portion of the coil, the coil further comprising a sacrificial link attached to the coil proximal end, the link being relatively more susceptible to electrolysis in an ionic solution than is the coil, said link connected to a core wire, advancing the coil through the catheter lumen, out the catheter tip and into the aneurysm, applying a positive electric current to the core wire to dissolve the link, and removing the core wire and catheter from the vessel.

18. The method of claim 17 wherein the coil comprises tantalum.

19. The method of claim 18 wherein the coil is at least partially covered with tantalum oxide.

20. The method of claim 17 wherein the core wire comprises platinum.

* * * * *